US00PP09590P

United States Patent [19]

Trees

[11] Patent Number: Plant 9,590

[45] Date of Patent: Jun. 18, 1996

[54] GERANIUM PLANT NAMED 'BFP-873 BRIGHT RED'

[75] Inventor: Scott C. Trees, Arroyo Grande, Calif.

[73] Assignee: Geo. J. Ball, Inc., West Chicago, Ill.

[21] Appl. No.: 465,223

[22] Filed: Jun. 5, 1995

[51] Int. Cl.[6] ..... A01H 5/00

[52] U.S. Cl. ..... Plt./87.12

[58] Field of Search ..... Plt./87.12

*Primary Examiner*—James R. Feyrer

*Attorney, Agent, or Firm*—Burns, Doane, Swecker & Mathis

[57] ABSTRACT

The new and distinct *Pelargonium×hortorum* cultivar named 'BFP-873 Bright Red' is provided. This new Zonal Geranium was the result of a controlled breeding program wherein the a plant designated 3804-1 (non-patented in the United States) was pollinated by the 'Fox' cultivar (U.S. Plant Pat. No. 7,083). The new cultivar forms attractive semi-double bright red florets. Medium green foliage is well retained during shipment. A medium self-branching growth habit is exhibited that does not require the use of a growth regulator.

1 Drawing Sheet

SUMMARY OF THE INVENTION

The present invention comprises a new and distinct Geranium cultivar, botanically known as *Pelargonium×hortorum* Bailey, and hereinafter is referred to by the cultivar name 'BFP-878 Bright Red'.

The new cultivar is a product of a planned breeding program which had the objective of the creation of a Geranium cultivar that exhibits uniform flowers, medium green foliage, a medium self-branching growth habit that requires no growth regulator, a propensity for rapid rooting, and stable foliage coloration during shipment.

The breeding program that resulted in the production of the new cultivar of the present invention was carried out in a controlled environment during 1992 at Arroyo Grande, Calif. U.S.A. The female parent (i.e., seed parent) was a plant designated 3804-1 (non-patented in the United States) which exhibits single scarlet florets with dark green foliage. The male parent (i.e., pollen parent) was the 'Fox' cultivar (U.S. Plant Pat. No. 7,083), which exhibits semi-double purple florets with medium green foliage. The parentage of the new 'BFP-873 Bright Red' cultivar can be summarized as follows:

3804-1×'Fox'.

'BFP-873 Bright Red' was discovered and selected during 1992 as a highly distinctive flowering plant from among the progeny of the stated cross at Arroyo Grande, Calif., U.S.A. This plant was initially designated BFP-873.

It was found that the new cultivar of the present invention:

(a) exhibits attractive semi-double bright red florets,
(b) forms medium green foliage; and
(c) exhibits a medium self-branching growth habit in the absence of a growth regulator.

When plant material of the 'BFP-873 Bright Red' cultivar is subjected to standard random amplified polymorphic DNA marker analysis (RAPD) using polymerase chain reaction (PCR) and a known set of DNA primers, it is found to exhibit a distinctive fingerprint map which is on file at the Ball FloraPlant Division of Geo J. Ball, Inc. at Arroyo Grande, Calif., U.S.A.

The first act of asexual reproduction of 'BFP-873 Bright Gold' cultivar was accomplished when vegetative cuttings were taken from the initial selection in a controlled environment at Arroyo Grande, Calif., U.S.A., by a technician working under the direction and supervision of the originator of the new cultivar. Horticultural examination of plants resulting from such asexual propagation during 1993 has demonstrated that the combination of unique characteristics as herein described for the 'BFP-873 Bright Red' cultivar is fixed and is retained through successive generations of such asexual reproduction.

The new 'BFP-873 Bright Red' cultivar has not been observed under all possible environmental conditions. Accordingly, the described phenotype may vary somewhat with variations in the environment, such as temperature, light intensity, and day length.

Of the many commercial cultivars, the 'BFP-420 Bright Red' cultivar (U.S. plant patent application Ser. No. 08/341,912, filed Nov. 15, 1994) is considered to be in the most similar to the new cultivar of the present invention. When the new cultivar of the present invention is compared to the 'BFP-420 Bright Red' cultivar, it is found that the 'BFP-873 Bright Red' cultivar exhibits umbels (e.g., approximately 9.0 to 10.5 cm. vs. approximately 9.0 to 9.5 cm.), smaller florets (e.g., approximately 4.2 to 4.7 cm. vs. approximately 5.0 to 5.1 cm.), and fewer florets per umbel (e.g., approximately 17 to 30 vs. approximately 30 to 36). The 'BFP-873 Bright Red' cultivar additionally exhibits a less compact growth habit and larger leaves as specified in greater detail hereafter.

The new cultivar of the present invention is being marketed by Geo. J. Ball, Inc. under the SATISFACTION trademark.

BRIEF DESCRIPTION OF THE PHOTOGRAPH

The accompanying photograph of FIG. 1 shows the general appearance of the overall plant of the new 'BFP-873 Bright Red' cultivar with colors being as nearly true as it is reasonably possible to make the same in a color illustration of this character. The plant was being grown in a greenhouse at West Chicago, Ill., U.S.A.

DETAILED DESCRIPTION

Figure 1:
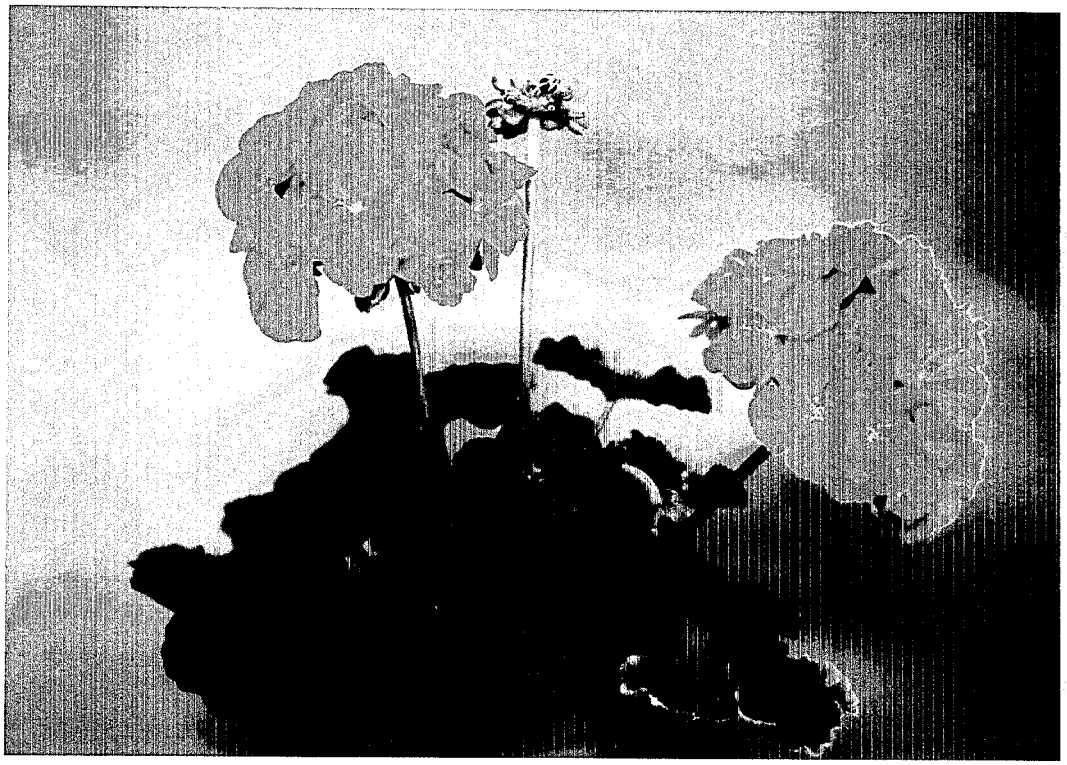

The following observations, measurements and comparisons describe plants grown in Ball FloraPlant's greenhouses located at West Chicago, Ill., U.S.A. under conditions which approximate those generally used in commercial practice. In the following description, color references are made to the R.H.S. Colour Chart of The Royal Horticultural Society, London, England. The color values were determined between 11:00 and 11:45 a.m. on Jan. 3, 1995, under natural light conditions of 2,000 footcandles.

Classification:

*Botanical.*—*Pelargonium×hortorum* Bailey, cv. 'BFP-873 Bright Red'.

*Commercial.*—Zonal Geranium.

INFLORESCENCE

A. Umbel:

*Average diameter.*—Approximately 9.0 to 10.5 cm. compared to approximately 9.0 to 9.5 cm. for the 'BFP-420 Bright Red' cultivar.

*Average depth.*—Approximately 6.0 to 7.5 cm. compared to approximately 5.0 to 7.0 cm. for the 'BFP-420 Bright Red' cultivar.

*Peduncle length.*—Approximately 15.0 to 17.5 cm. compared to approximately 13.5 to 18.0 cm for the 'BFP-420 Bright Red' cultivar.

*Pedicel length.*—Approximately 1.5 to 2.5 cm. compared to approximately 2.4 to 2.7 cm. for the 'BFP-420 Bright Red' cultivar.

*Number of umbels plant.*—When grown in a 10 cm. pot at 9 weeks after the sticking of a rooted cutting, there commonly are approximately 3 to 5 umbels per plant. The 'BFP-420 Bright Red' cultivar commonly forms approximately 3 to 6 umbels per plant.

*Number of florets umbel.*—When grown 10 cm. pots at 9 weeks, approximately 17 to 30 florets per umbel commonly are formed. This compares to approximately 30 to 36 florets per umbel for the 'BFP-420 Bright Red' cultivar under the same growing conditions.

B. Corolla:

*Average diameter.*—Approximately 4.2 to 4.7 cm. compared to approximately 5.0 to 5.1 cm. for the 'BFP-420 Bright Red' cultivar.

*Form.*—Both the 'BFP-873 Bright Red' cultivar and the 'BFP-420 Bright Red' cultivar are semi-double with petaloids.

*Number of petaloids.*—Commonly forms 3 to 4 petaloids per floret whereas the 'BFP-420 Bright Red' cultivar commonly possesses 2 to 3 petaloids per floret.

*Color.*—General tonality from a distance of three meters: Red. Adaxial: Closest to Red Group 46B. This compares to Red Group 44B for the 'BFP-420 Bright Red' cultivar. Abaxial: Red Group 46C. This compares to Red Group 43B for the 'BFP-420 Bright Red' cultivar.

C. Bud:

*Shape.*—Oval.

*Color.*—Adaxial: Red Group 46B compared to Red Group 44B for the 'BFP-420 Bright Red' cultivar. Abaxial: Red Group 46C compared to Red Group 43B for the 'BFP-420 Bright Red' cultivar.

D. Reproductive organs:

*Androecium.*—The anthers commonly approximately 2.0 mm. in length. The pollen color commonly is Orange-Red Group 31A for both the 'BFP-873 Bright Red cultivar and the 'BFP-420 Bright Red' cultivar. The filaments are approximately 6.0 to 9.0 mm in length.

*Gynoecium.*—The pistil length commonly is approximately 10.0 mm. There is a single stigma which commonly has a length of approximately 5.0 mm. which commonly branches into 5 parts, and the style length is approximately 5.0 mm.

*Fertility.*—Commonly does not produce fruits in the absence of mechanical fertilization.

E. Spring flowers response period.—Approximately 6 to 7 weeks from rooted cuttings under standard greenhouse conditions.

F. Outdoor flower production: Freely flowering under outdoor growing conditions with substantially continuous blooming.

G. Durability: Ships well.

PLANT

A. Foliage: Medium green.

*Form.*—Reniform, with cordate base.

*Margin.*—Crenate.

*Color.*—Adaxial: Yellow-Green Group 147B. This compares to Yellow-Green Group 147A with a zone of Yellow-Green Group 146A for the 'BFP-420 Bright Red' cultivar. Abaxial: Yellow-Green Group 147C for both the 'BFP-873 Bright Red' cultivar and the 'BFP-420 Bright Red' cultivar.

*Size.*—Approximately 9.7 to 10.5 cm. at the widest point and approximately 8.0 to 9.2 cm. at the narrowest point. This compares to approximately 8.5 to 9.5 cm. at the widest point and approximately 7.0 to 7.6 cm. at the narrowest point for the 'BFP-420 Bright Red' cultivar.

B. General appearance and form:

*Internode length.*—Commonly varies from approximately 1.3 to 1.6 cm. This compares to approximately 2.0 to 2.5 cm. for the 'BFP-420 Bright Red' cultivar.

*Branching pattern.*—Freely basal branching. No pinching is required to obtain self-branching. A vigorous self-branching growth habit is observed in the absence of a growth regulator.

*Height.*—Approximately 28 to 32 cm. above a 10 cm. pot at 9 weeks under standard greenhouse conditions. This compares to approximately 25 to 30 cm. for the 'BFP-420 Bright Red' cultivar.

I claim:

1. A new and distinct Geranium cultivar named 'BFP-873 Bright Red', substantially as herein shown and described, which:

(a) exhibits attractive semi-double bright red florets,
(b) forms medium green foliage, and
(c) exhibits a medium self-branching growth habit in the absence of a growth regulator.

* * * * *